US011255864B2

(12) United States Patent
Soederlund et al.

(10) Patent No.: US 11,255,864 B2
(45) Date of Patent: Feb. 22, 2022

(54) DETECTION OF A BIOMARKER IN A SAMPLE OF A FLOWABLE SUBSTANCE

(71) Applicant: CALMARK SWEDEN AB, Karlstad (SE)

(72) Inventors: Anna Soederlund, Arsta (SE); Ana Catarina De Araújo Silva, Nacka (SE); Johan Gustav Svahn, Laerbo (SE); Sebastian De Arteaga, Arsta (SE); Michael Lundh, Lund (SE); Karl Sivert Anders Soederbaerg, Norrtaelje (SE); Nils Olof Eriksson, Enskede (SE)

(73) Assignee: CALMARK SWEDEN AB, Karlstad (SE)

( * ) Notice: Subject to any disclaimer, the term of this patent is extended or adjusted under 35 U.S.C. 154(b) by 452 days.

(21) Appl. No.: 16/477,143

(22) PCT Filed: Jan. 9, 2018

(86) PCT No.: PCT/EP2018/050424
§ 371 (c)(1),
(2) Date: Jul. 10, 2019

(87) PCT Pub. No.: WO2018/130506
PCT Pub. Date: Jul. 19, 2018

(65) Prior Publication Data
US 2019/0353670 A1 Nov. 21, 2019

(30) Foreign Application Priority Data
Jan. 13, 2017 (SE) .................. 1750028-1

(51) Int. Cl.
G01N 33/72 (2006.01)
G01N 21/78 (2006.01)
(Continued)

(52) U.S. Cl.
CPC ........... *G01N 33/726* (2013.01); *G01N 21/78* (2013.01); *G01N 33/68* (2013.01); *G01N 2001/002* (2013.01); *G01N 2021/1776* (2013.01)

(58) Field of Classification Search
CPC ........ A61B 2560/0462; A61B 5/14552; G01N 2001/002; G01N 2021/1776; G01N 21/78;
(Continued)

(56) References Cited

U.S. PATENT DOCUMENTS

| 5,208,163 A | 5/1993 | Charlton et al. |
| D428,654 S | 7/2000 | Schlesinger et al. |

(Continued)

FOREIGN PATENT DOCUMENTS

| WO | WO-2003/020424 A1 | 3/2003 |
| WO | WO-2005/084527 A1 | 9/2005 |

(Continued)

OTHER PUBLICATIONS

Notice of Allowance and Fee(s) Due for U.S. Appl. No. 35/508,180, filed Dec. 7, 2020, (9 pages), United States Patent and Trademark Office, U.S.
(Continued)

Primary Examiner — Jennifer Wecker
Assistant Examiner — Kathryn Elizabeth Limbaugh
(74) Attorney, Agent, or Firm — Alston & Bird LLP

(57) ABSTRACT

In the detection of the presence of a biomarker or the like in a sample of a flowable substance, e.g. a powder or a liquid, usually a body fluid, such as blood, urine, or saliva, for example, a disposable sample receiver (3) is used, which has a receiving chamber (301) that is dimensioned to receive a predetermined volume and is surrounded by a depression (303) receiving any excess volume for which there is no
(Continued)

room in the receiving chamber (301). The receiving chamber (301) has a bottom outlet (302) closed by a removable strip (33), e.g. a plastic strip or foil. Upon pulling away the strip (33) from the bottom outlet, the sample in the receiving chamber is emptied into a flow path (32) leading to at least one detection compartment (321) permitting direct visual inspection. Preferably, disposable sample receiver (3) is used in a detector assembly (1) including an electronic camera (23), a CPU (26) and a display (22). Hereby, the volume of the sample to be analyzed will always be the same, and by controlling the exact point of time when the sample is passed on into the flow path (32), a high degree of repeatability and accuracy is achieved, and thereby also a fail-safe system.

22 Claims, 4 Drawing Sheets

(51) Int. Cl.
  *G01N 33/68* (2006.01)
  *G01N 1/00* (2006.01)
  *G01N 21/17* (2006.01)

(58) Field of Classification Search
  CPC ...... G01N 33/68; G01N 33/726; G01N 33/48; G01N 33/72; B01L 2200/06
  See application file for complete search history.

(56) References Cited

U.S. PATENT DOCUMENTS

| | | | |
|---|---|---|---|
| D589,614 S | 3/2009 | Cook et al. | |
| D609,801 S | 2/2010 | Egorov et al. | |
| D689,614 S | 9/2013 | Browne et al. | |
| D694,889 S | 12/2013 | Karlsson et al. | |
| D702,355 S | 4/2014 | Laplante et al. | |
| D725,768 S | 3/2015 | Eustis et al. | |
| D741,497 S | 10/2015 | Aber et al. | |
| D743,035 S | 11/2015 | Uozumi et al. | |
| 9,228,953 B2 | 1/2016 | Karlsson et al. | |
| 9,421,322 B2 | 8/2016 | Breitweiser et al. | |
| 9,950,135 B2 | 4/2018 | Winter | |
| D822,217 S | 7/2018 | Sebban | |
| D854,169 S | 7/2019 | Briante et al. | |
| D854,187 S | 7/2019 | Meindl et al. | |
| D882,753 S | 4/2020 | de Araujo Silva et al. | |
| 2002/0001852 A1 | 1/2002 | Mendel-Hartvig et al. | |
| 2002/0110496 A1 | 8/2002 | Samsoondar | |
| 2004/0156037 A1 | 8/2004 | Mawhirt et al. | |
| 2006/0222567 A1 | 10/2006 | Kloepfer et al. | |
| 2016/0100783 A1 | 4/2016 | Ivosevic et al. | |
| 2018/0143210 A1* | 5/2018 | Ayyub | A61K 31/216 |

FOREIGN PATENT DOCUMENTS

| | | |
|---|---|---|
| WO | WO-2005/086744 A2 | 9/2005 |
| WO | WO-2013/077802 A1 | 5/2013 |
| WO | WO-2014/043528 A1 | 3/2014 |
| WO | WO-2016/176366 A1 | 11/2016 |

OTHER PUBLICATIONS

International Searching Authority, International Search Report and Written Opinion for International Application No. PCT/EP2018/050424, dated Feb. 26, 2018, 13 pages, The Netherlands.

Ouyang et al., Multilevel Fluidic Flow Control In A Rotationally-Driven Polyester Film Microdevice Created Using Laser Print, Cut and Laminate, Lab On A Chip, vol. 16, No. 2, Jan. 1, 2016, pp. 377-387. DOI: 10.1039/C5LC01332A.

Calmark's Products. (online), (4 pages), (date unknown). [Retrieved from the Internet Feb. 13, 2020] <https://www.calmark.se/eng/products>.

* cited by examiner

DETECTION OF A BIOMARKER IN A SAMPLE OF A FLOWABLE SUBSTANCE

CROSS REFERENCE TO RELATED APPLICATIONS

This application is a National Stage Application, filed under 35 U.S.C. § 371, of International Application No. PCT/EP2018/050424, filed Jan. 9, 2018, which application claims priority to and the benefit of Swedish Application No. 1750028-1, filed Jan. 13, 2017; the contents of both of which as are hereby incorporated by reference in their entirety.

BACKGROUND

Related Field

The present invention relates to a method of detecting the presence of a biomarker in a sample of a flowable substance.

Further, it relates to a disposable sample receiver for use in detection of the presence of a biomarker in a sample of a flowable substance, said disposable sample receiver including a receiving chamber for reception of the sample of flowable substance, a bottom outlet from the receiving chamber, a flow path leading away from the bottom outlet.

In addition, it relates to a detector assembly for use in detection of the presence of a biomarker in a sample of a flowable substance, said assembly including a portable detector housing having a place for reception of a disposable sample receiver, and a disposable sample receiver adapted to be located in said place.

Description of Related Art

U.S. Pat. No. 9,228,953 B2 (Karlsson et al.) discloses a testing system for assessing the level of a biochemical marker, comprising a disposable device with a sample inlet and a at least one visible detection compartment, provided with composition including a chemical means for direct detection of said biochemical marker. To assess the level of the biomarker, the disposable device is placed in a housing that also has a support surface for a smartphone. After the detection of the biomarker, the smartphone takes a digital picture, which is transmitted via internet to a server that runs a dedicated program to analyze the picture and the retransmits the result to the smartphone.

In US '953, the disposable device has a sample inlet in the form of a sample inlet connected to a chamber adapted to receive a capillary device containing a sample arranged to be placed onto a receiving device, e.g. a plasma separation device, i.e. a filter. The disposable device is supplied with test blood by means of a capillary device being filled with the sample, e.g. a whole blood amounting to 1-100 µl, suitably 25-75 µl, and preferably about 50 µl. However, if desired the blood may be added by a pipette releasing a drop of the sample. The plasma is made to flow (by negative pressure or by capillary force) through a filter and into a collection chamber, from where it proceeds through a microfluidic channel into at least one detection compartment having a volume of 0.1-15 µl, more preferred 3-10 µl, and most preferred 4-9 µl.

BRIEF SUMMARY

The object of the present invention is to provide a fail proof system for detection of the presence of a biomarker in a sample of a flowable substance.

In a first aspect of the present invention, this object is achieved in a method of detecting the presence of a biomarker in a sample of a flowable substance, comprising:
a) providing a disposable sample receiver having a receiving chamber, a bottom outlet from the receiving chamber, a flow path leading away from the bottom outlet;
b) disposing the sample in the receiving chamber and permitting the flowable substance to pass through the bottom outlet into the flow path;
c) providing a depression surrounding the receiving chamber;
d) filling the receiving chamber until an excess of the flowable substance spills over into the depression; and
e) emptying the receiving chamber by removing from the bottom outlet a separating member that is impermeable to the flowable substance, which separating member has prevented flow from the receiving chamber through the bottom outlet and into the flow path.

By filling the receiving chamber until an excess of the flowable substance spills over into the depression, the volume of the sample to be analyzed will always be the same, and by controlling the exact point of time when the sample is passed on into the flow path (by removing the separating member from the bottom outlet of the receiving chamber) a high degree of repeatability and accuracy is achieved, and thereby also a fail-safe system.

To facilitate the detection, it is preferred that the flow path comprises a permeable member, which prevents passage of at least one component of the flowable substance but permits passage of another one.

It is also preferred that the disposable sample receiver comprises a directly visible detection compartment located at the opposite end of said flow path compared to the bottom outlet, and that the detection compartment is provided with a reagent which shifts color upon presence of a biomarker in the sample of flowable substance.

In the present context, the expression "directly visible detection compartment" is to be defined as a detection compartment, which a user can see from the outside of the sample receiver. This means, as an example, that a user can inspect the color in the detection compartment with the naked eye.

It is to be understood that "a biomarker" is to be interpreted as "at least one biomarker". It is further understood that "a biomarker" is a measurable indicator of some biological state or condition.

Said detection compartment may be prepared with a reagent composition, e.g. arranged to react with one or more of the following biochemical markers, all of which may be present in plasma: LDH, Hemoglobin (Hb), aspartate aminotransferase (AST), alanine aminotransferase (ALT), lactate, Creatinine Kinase (CK), Creatinine, Amylasis (PIA), C-reactive protein (CRP), Hydrogen ion concentration (pH), Albumin, K, Mg and Ca. It is to be understood that the examples mentioned above are by no means limiting to the basic principles of the invention.

Although the flowable substance usually is a liquid, e.g. various body fluids, it could also be a powder. It is expected that in most cases the flowable substance will be blood, and that the permeable member, which usually is a filter, separates blood cells from plasma containing the biomarker. Thereby, a simple and accurate detection of the biomarker can be carried out.

In some cases, it may be desired to control the volume and timing of a flowable substance (i.e. secure that an exact volume is used as well as controlling the exact time when said volume is transferred) without detecting a biomarker.

For instance this may be the case if the flowable substance is in the form of a powder. In such cases, said permeable member may not be needed.

The detection compartment may or may not be prepared with a reagent.

In some cases, the user may detect a biomarker without the need for any reagent by merely inspecting the hue of the filter after that a sample has entered the detection compartment, as is the case e.g. with bilirubin which, if present, will result in the filter acquiring a yellowish color.

An operator may use visual inspection to analyze the color shift, but preferably the color shift is analyzed by an electronic camera and software, and the result is shown on a display. Thereby it is easy to save the result for later inspection and/or comparison.

In a second aspect of the present invention, the above object is achieved in that a disposable sample receiver of the kind stated in the second paragraph above comprises:
a) a depression surrounding the receiving chamber that is dimensioned to receive a predetermined volume, said depression receiving any excess volume for which there is no room in the receiving chamber; and
b) a removable separating member impermeable to the flowable substance and disposed at the bottom outlet to keep the bottom outlet sealed, said separating member upon removal connecting the receiving chamber to the flow path.

As the receiving chamber is dimensioned to receive a predetermined volume and is surrounded by a depression, the receiving chamber can be filled until an excess of the flowable substance spills over into the depression, whereby the volume of the sample to be analyzed will always be the same. Further, as the exact point of time when the sample is passed on to the flow path (by removing the separating member from the bottom outlet of the receiving chamber) can be controlled, a high degree of repeatability and accuracy is achieved, and thereby also a fail-safe system.

It is preferred that the disposable sample receiver comprises a directly visible detection compartment located at the opposite end of said flow path compared to the bottom outlet. As pointed out above, in the present context, the expression "directly visible detection compartment" is to be defined as a detection compartment, which a user can see from the outside of the sample receiver. This means, as an example, that a user can inspect the color in the detection compartment with the naked eye.

To facilitate the detection, it is preferred that the flow path at least upstream of the detection compartment is provided with a permeable member, which prevents passage of at least one component of the flowable substance but permits passage of another one.

Further, it is preferred that a reagent, which shifts color upon presence of a biomarker, is provided in said flow path, and that the reagent is located in or downstream of the permeable member.

In most cases, said permeable member is a filter member that may include a plurality of individual filters. As pointed out above, although the flowable substance usually is a liquid, e.g. various body fluids, it could also be a powder. It is expected that in most cases the flowable substance will be blood, and that the permeable member, which usually is a filter, separates blood cells from plasma containing the biomarker. Then, the reagent suitably is located in or downstream of the permeable member. Thereby, matter that might make it difficult to assess the color shift of the reagent will be prevented from reaching the reagent, and a simple and accurate detection of the biomarker can be carried out.

Then, it is preferable that the permeable member includes an uppermost receiving filter, at least one separation filter, and a lowermost detection filter, which contains the reagent and is located in the detection compartment. Such a filter assembly will prevent any unwanted matter from reaching the reagent, and any color change looked for will be easy to ascertain.

The filter/s can be of different types, exemplified but not limited to, blood separation filters, filters for separation by size, filters for affinity, capture or binding of specific components in the fluid to be filtered. The filters may be made of natural or synthetic material, or a combination thereof, and be of symmetric or asymmetric type.

In a third aspect of the present invention, the above object is achieved in that in a detector assembly of the kind stated in the third paragraph above said disposable sample receiver comprises:
a) a receiving chamber for reception of the sample of flowable substance, a bottom outlet from the receiving chamber, a flow path leading away from the bottom outlet, and in the flow path at least one of a reagent, which shifts color upon presence of the biomarker, and a permeable member, which prevents passage of at least one component of the flowable substance but permits passage of another one, said disposable sample receiver further comprising:
  aa) a depression surrounding the receiving chamber that is dimensioned to receive a predetermined volume, said depression being adapted to receive any excess volume for which there is no room in the receiving chamber; and
  ab) a removable separating member impermeable to the flowable substance and disposed at the bottom outlet to keep the bottom outlet sealed, said separating member upon removal from the bottom outlet connecting the receiving chamber to the flow path; and
said detector housing comprises:
b) a device for removing the separating member from the bottom outlet of the receiving chamber to activate the disposable sample receiver.

As the receiving chamber is dimensioned to receive a predetermined volume and is surrounded by a depression, the receiving chamber can be filled until an excess of the flowable substance spills over into the depression, whereby the volume of the sample to be analyzed will always be the same. Further, as the detector housing comprises a device for removing the separating member from the bottom outlet of the receiving chamber, the exact point of time when the sample is passed on to the reagent (by removing the separating member from the bottom outlet of the receiving chamber) can be controlled, a high degree of repeatability and accuracy is achieved, and thereby also a fail-safe system.

It is preferred that the disposable sample receiver comprises a directly visible detection compartment located at the opposite end of said flow path compared to the bottom outlet. As pointed out above, in the present context, the expression "directly visible detection compartment" is to be defined as a detection compartment, which a user can see from the outside of the sample receiver. This means, as an example, that a user can inspect the color in the detection compartment with the naked eye.

To facilitate the detection, it is preferred that the flow path at least upstream of the detection compartment is provided with a permeable member, which prevents passage of at least one component of the flowable substance but permits passage of another one.

Further, it is preferred that a reagent, which shifts color upon presence of a biomarker, is provided in said flow path, and that the reagent is located in or downstream of the permeable member.

The permeable member suitably is a filter member that may include a plurality of individual filters. Further, although the flowable substance usually is a liquid, e.g. various body fluids, it could also be a powder. It is expected that in most cases the flowable substance will be blood, and that the permeable member, which usually is a filter, separates blood cells from plasma containing the biomarker. Then, the reagent suitably is located in or downstream of the permeable member. Thereby, matter that might make it difficult to assess the color shift of the reagent will be prevented from reaching the reagent, and a simple and accurate detection of the biomarker can be carried out.

Then, it is preferable that the permeable member includes an uppermost receiving filter, at least one separation filter, and a lowermost detection filter, which contains the reagent. Such a filter assembly will prevent any unwanted matter from reaching the reagent.

Even though the color shift of the reagent can be assessed by visual inspection, it is preferred that the detector housing comprises equipment for analyzing color change marks of the biomarker to be detected, and said equipment includes an electronic camera, software, and a display for displaying the result of the analysis. Thereby it is easy to save the result for later inspection and/or comparison.

Suitably, the disposable sample receiver includes a top member and a bottom member. Further, the top member has wall portions defining side walls of the receiving chamber, and the removable separating member is an elongate strip having one end closing the bottom outlet by forming a bottom of the receiving chamber and the other end fixed to a body portion of the disposable sample receiver. In addition, the disposable sample receiver has an internal support for the strip, and the internal support is spaced from the fixed end of the strip to form between them a space under the strip. The space has a depth that is sufficient to permit the strip to be pressed into the space a distance that will pull the strip away from the bottom outlet to empty the sample of flowable substance into the flow path. Thereby, a simple and reliable mechanism for opening the bottom outlet of the receiving chamber at an identifiable point of time is obtained.

It is preferred that the top member of the disposable sample receiver has an opening located above the space, and that a device for pulling the sealing end of the strip away from the bottom outlet includes a pivotal member on the detector housing provided with a protrusion adapted to enter the opening in order to press down the strip to remove it from the bottom outlet and thereby let the flowable substance flow into the flow path.

Suitably, the pivotal member is a lid that on shutting will cover the disposable sample receiver and simultaneously pull away the strip from the bottom outlet to let the sample of flowable substance flow into the flow path, whereby every sample to be analyzed will be subjected to the same testing conditions with regard to volume and timing.

BRIEF DESCRIPTION OF THE FIGURES

In the following, the invention will be described in more detail with reference to preferred embodiments and the appended drawings.

DETAILED DESCRIPTION OF VARIOUS EMBODIMENTS

Figure 1:
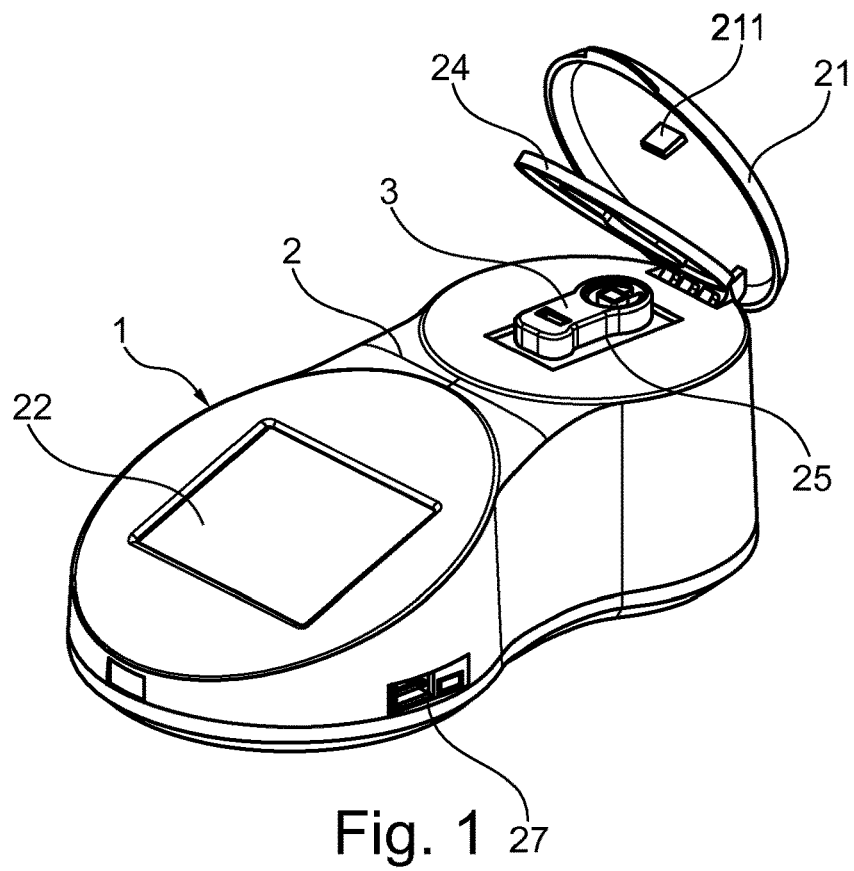
FIG. 1 is an isometric view of a preferred embodiment of a detector assembly of the invention, including a detector housing and a disposable sample receiver.

The detector assembly 1 shown in FIG. 1 is a preferred embodiment of the present invention and is adapted for use in detection of the presence of a biomarker in a sample of a flowable substance, which usually is a body fluid, such as whole blood, urine, and saliva, for example. The assembly 1 includes a portable detector housing 2 having a place 25 for reception of a disposable sample receiver 3. It further includes a disposable sample receiver 3 adapted to be located in said place 25.

Figure 3:
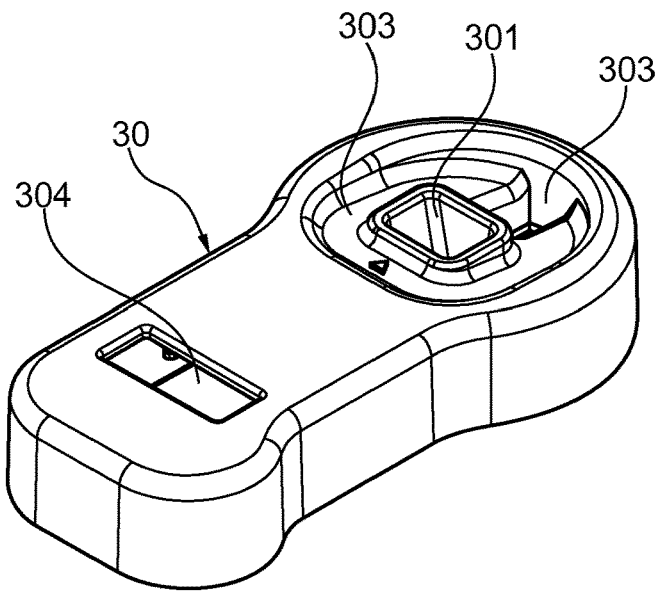
FIG. 3 is an isometric view of a top member of the disposable sample receiver of FIG. 1.
Figure 4:
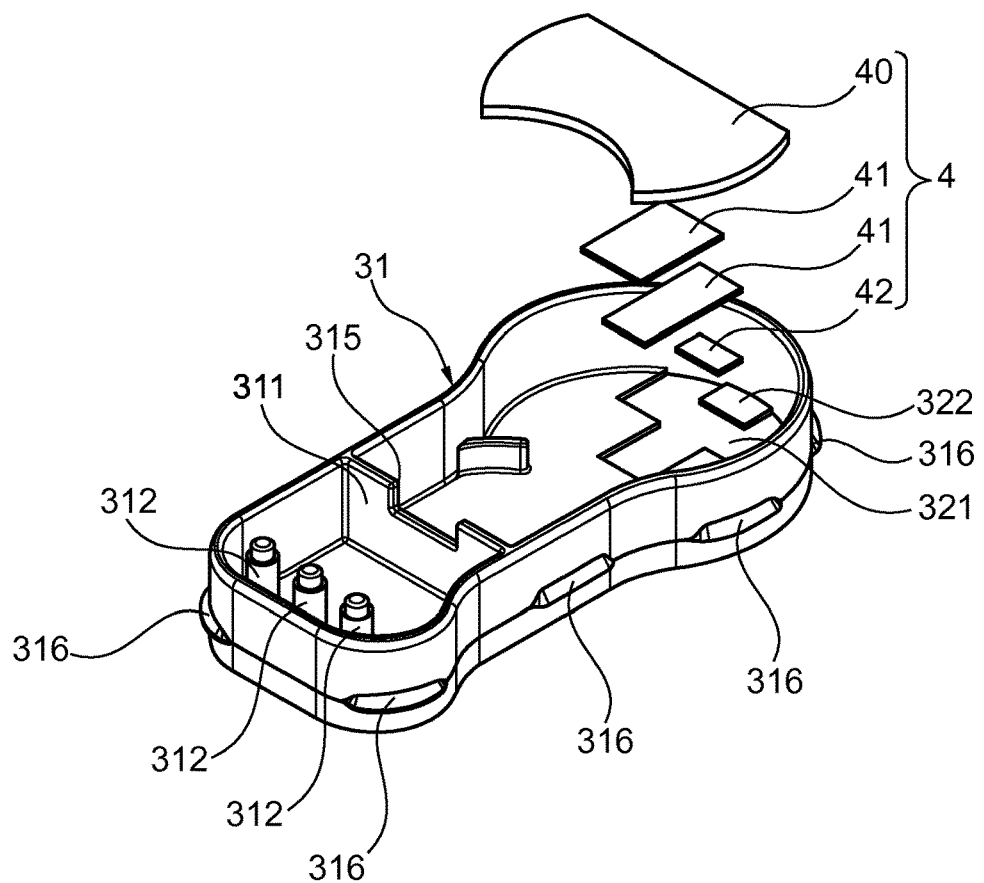
FIG. 4 is an isometric view of a bottom member of the disposable sample receiver of FIG. 1 and also shows an exploded view of a filter assembly that may be located in the bottom member.
Figure 5:
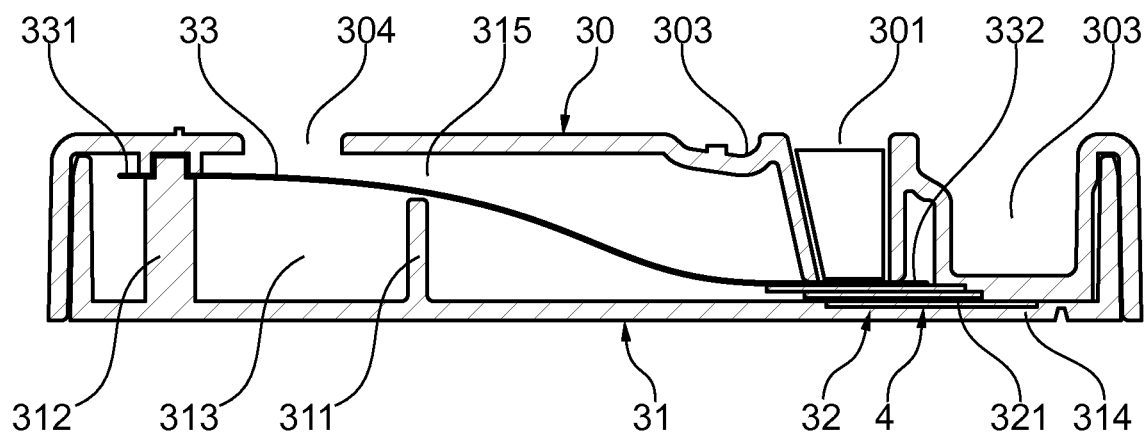
FIG. 5 is a schematic longitudinal cross-sectional view of the disposable sample receiver of FIG. 1 showing inter alia a removable separating member in the shape of a strip having one end fixed to the receiver body and the other end sealing against a bottom outlet of a chamber for receiving the sample.
Figure 6:
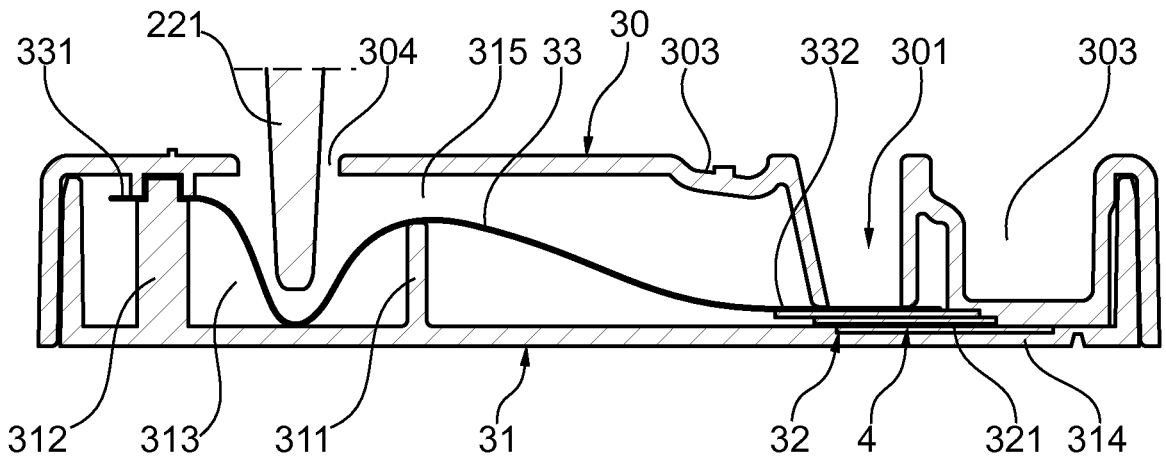
FIG. 6 is a view similar to FIG. 5 but showing how the removable separating member is removed from the bottom outlet to open the bottom outlet, so that the receiving chamber is emptied and part of the sample has arrived at the reactant for detection of the biomarker.
Figure 7:
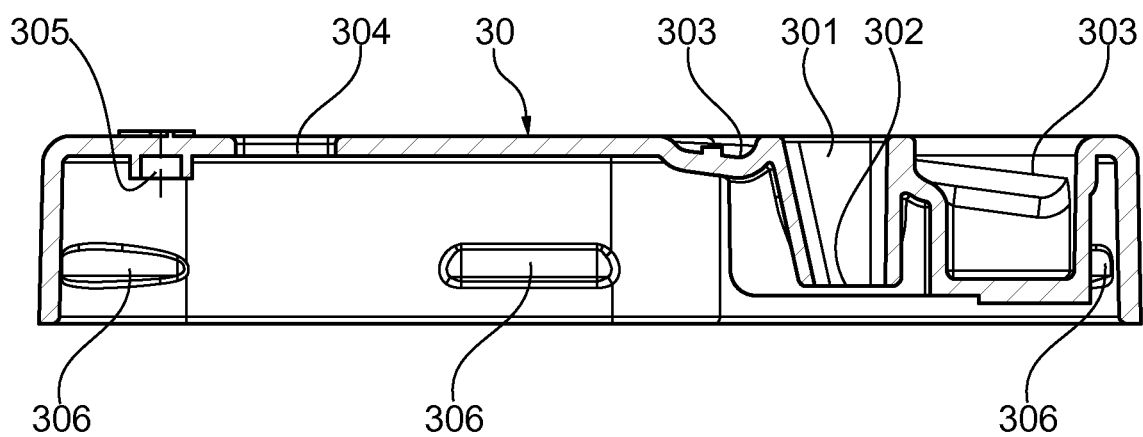
FIG. 7 is a longitudinal cross-sectional view of the top member of the disposable sample receiver of FIG. 1 showing a depression surrounding the receiving chamber.
Figure 8:
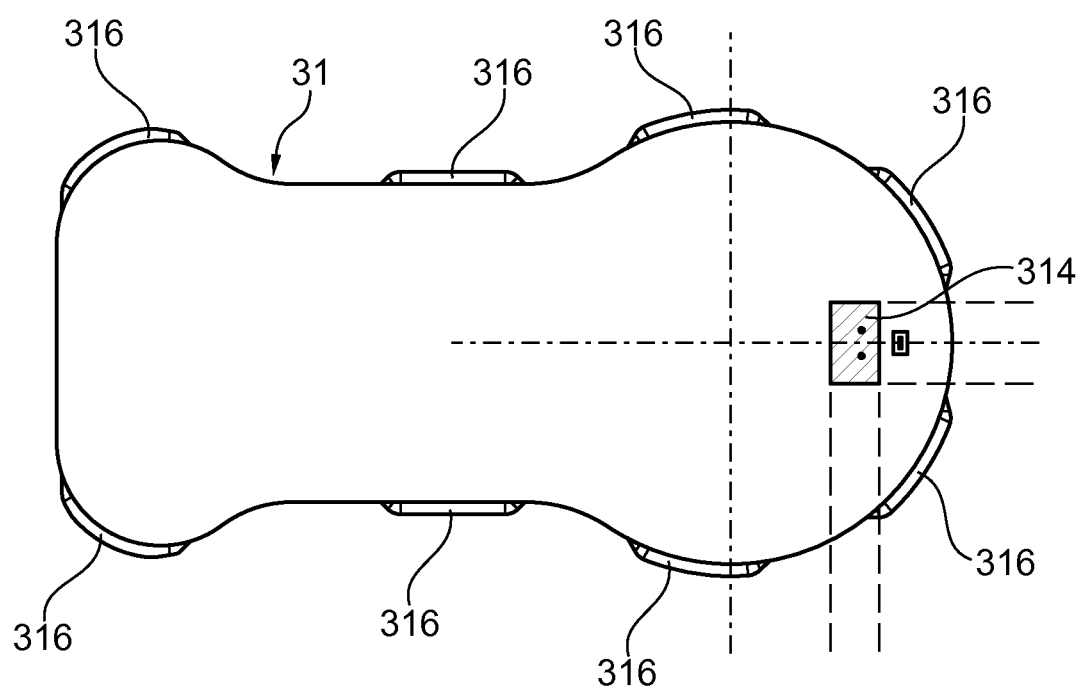
FIG. 8 is a view of the underside of the bottom member of the disposable sample receiver of FIG. 1 showing a transparent window for inspection of a change of color in the reactant.

The disposable sample receiver 3 has a top member 30 shown in FIG. 3 and a bottom member 31 shown in FIG. 4. The top member 30 fits tightly on bottom member 31. FIG. 8 shows that the bottom member 31 on the outside of its wall has a plurality of locking projections 316, which are adapted to cooperate with a corresponding number of locking indentations 306 on the inside of the wall of the top member 30 shown in FIG. 7. Together, the projections 316 and the indentations 306 form snap locks. As is best shown in FIGS. 5-7, the top member 30 has a receiving chamber 301 for reception of the sample of flowable substance, and a bottom outlet 302 from the receiving chamber 301. When the top member 30 is fixed on the bottom member 31, a flow path 32 leading away from the bottom outlet 302 is defined between the top member 30 and the bottom member 31. A depression 303 surrounds the receiving chamber 301 that is dimensioned to receive a predetermined volume. The depression 303 is adapted to receive any excess volume for which there is no room in the receiving chamber 301. Thereby the analyzed amount of the sample is exactly the same each time an analysis is carried out.

As is best shown in FIGS. 5 and 6, the disposable sample receiver 3 further has a removable separating member 33 that is impermeable to the flowable substance and disposed at the bottom outlet 302 to keep the bottom outlet 302 sealed. Upon removal separating member 33 from the bottom outlet 302, the receiving chamber 321 is connected to the flow path 32, at the end of which a detection compartment 321 is located. In the embodiment shown in FIGS. 5 and 6, the detection compartment 321 is formed by a recess in the bottom member 31. If desired, the flow path 32 may split into a plurality of branches (not shown) and every branch has its own separate detection compartment 321.

In the preferred embodiment shown in FIGS. 5 and 6, the removable separating member 33 is an elongated strip, which according to one, non-limiting example is a substantially T-shaped plastic foil. One end 332 of the strip or foil 33 closes the bottom outlet 302 by forming a bottom of the receiving chamber 301, and the other end 331, i.e. the top portion of the "T", is fixed to a body portion 305, 312 of the disposable sample receiver 3. In the preferred embodiment shown in FIGS. 4-6, the body portion 312 is formed by three posts extending upward from the bottom of the bottom member 31. The top of each post 312 has a reduced diameter, and the fixed end 333 of the removable strip or foil 33 has three matching holes for securing the fixed end 331 of the strip or foil 33 to the tops of the posts 312. To secure the strip or foil 33 to the posts 312, the top member 30 suitably is provided internally with three sockets 305 adapted to fit on the tops of the three posts 312.

Said elongated strip 33 may be of various materials, however according to one example it is made of 12 μm thick Hostaphan® WN from "Mitsubishi polyester film", which is a translucent white film made of polyester, e.g. polyethylene terephthalate (PET) with high dielectric strength and large volume resistance and which can be easily formed in both warm and cold states.

Another conceivable example is 0.19 μm thick Mylar® A polyethyleneterephtalate-based transparent, flexible polyester film from Synflex, which is impervious to moist and solvents.

Both of the above examples of suitable materials for said elongated strip 33 provides impervious, yet flexible and pliable film materials which both prevents the flowable substance from exiting via the outlet 302, and also is flexible enough to be pulled away from the outlet. The skilled person understands that the above mentioned materials are merely two examples out of many, and that many other kinds of materials may be equally suitable for said elongated strip 33. The pulling away of the strip from the outlet will now be described in more detail.

FIGS. 4-6 also show that the bottom member 31 of the disposable sample receiver 3 further has an internal transversal support 311 for the strip 33. The internal support 311 is spaced from the fixed end 331 of the strip or foil 33 to form between them a space 313 under the strip or foil 33. The space 313 has a depth that is sufficient to permit the strip or foil 33 to be pressed into the space 313 a distance that will pull the sealing end 332 of the strip or foil 33 away from the bottom outlet 302 in order to empty the sample of flowable substance into the flow path 32 as illustrated in FIG. 6. As shown in FIG. 4, it is preferred that the internal support 311 is a transversal wall having at its top a recess 315 of a width and a depth that makes it suitable for guiding the strip or foil 33. Preferably, the strip or foil 33 is of a thickness that is sufficient to make it self-supporting but yet pliable enough to be pressed down into the space 313 to open the bottom outlet 302.

To press the strip or foil 33 into the space 313 as shown in FIG. 6, it is preferred that the top member 30 of the disposable sample receiver 3 has an opening 304 located above the space 313. Then, as shown in FIG. 1, it is also preferred that a device for pulling the sealing end 332 of the strip or foil 33 away from the bottom outlet 302 of the receiving chamber 301 includes a pivotal member 21 located on the detector housing 2 and provided with a protrusion 211 adapted to enter the opening 304 in order to press down the strip or foil 33 to remove it from the bottom outlet 302 and thereby let the flowable substance flow into the flow path 32.

Figure 2:
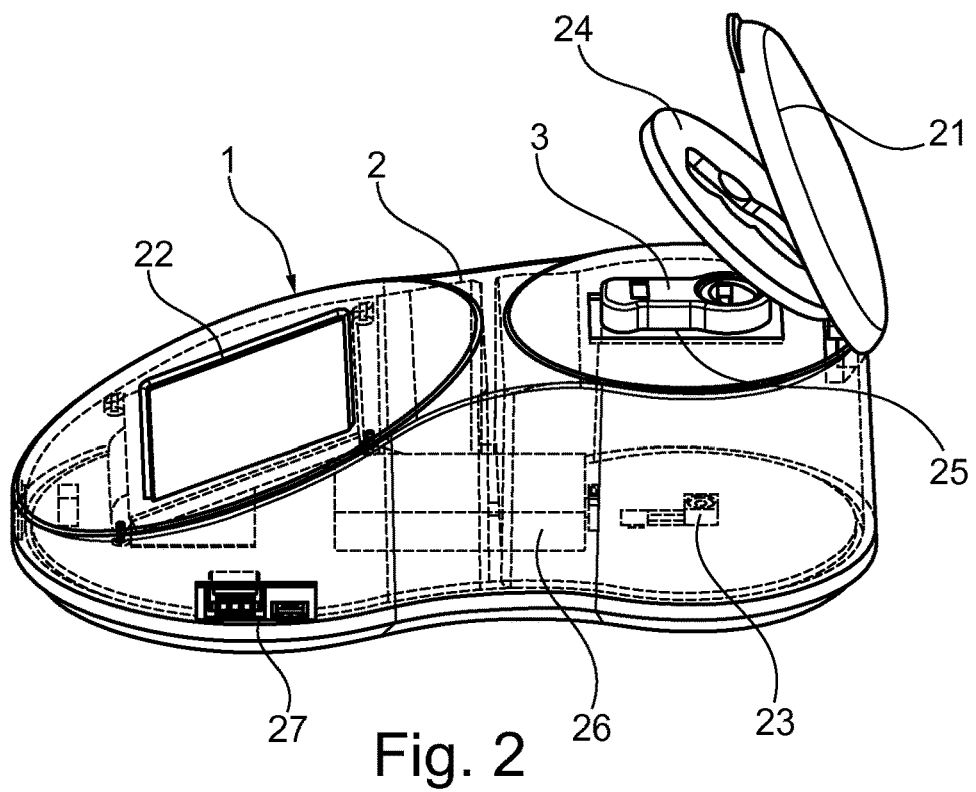
FIG. 2 is an isometric view of the detector assembly of FIG. 2 from a slightly different angle and with a portion of the housing made transparent for showing its interior.

In the preferred embodiment shown in FIG. 1, the pivotal member is a lid 21 that on shutting will cover the disposable sample receiver 3 and simultaneously pull away the strip 33 from the bottom outlet 302 to let the sample of flowable substance flow into the flow path 32, whereby every sample to be analyzed will be subjected to the same testing conditions with regard to volume and timing. Further, in the embodiment shown in FIG. 1 the detector assembly 1 has a separate pivotal locating lid 24 mounted under lid 21. As is best shown in FIG. 2, the locating lid 24 has an opening of a shape that matches the outer contour of the disposable sample receiver 3 to hold the sample receiver in an exact predetermined position on place 25, which in the shown embodiment is rectangular and larger than the disposable sample receiver 3.

At least upstream of the detection compartment 321, the flow path 32 preferably is provided with a permeable member 4, which prevents passage of at least one component of the flowable substance but permits passage of another one. In most cases said permeable member 4 suitably is a filter member that may include a plurality of individual filters. As pointed out above, although the flowable substance usually is a liquid, e.g. various body fluids, it could also be a powder. It is expected that in most cases the flowable substance will be blood, and that the permeable member 4, which usually is a filter, separates blood cells from plasma possibly containing a biomarker. If desired, the permeable member 4 may be a single filter member, for example. However, in the preferred embodiment of FIG. 4 it is a filter assembly 4 shown in an exploded view and comprising an uppermost receiving filter 40, at least one separation filter 41, and lowermost detection filter 42 that is adapted to be located in the detection compartment 321. As shown in FIG. 4, an end portion of the detection compartment 321 may be wider than the lowermost detection filter 42 to receive the component of the flowable substance that has passed through the entire filter assembly 4. The detection compartment 321 has a stop 322 to assist in the correct positioning of the lowermost detection filter 42. The filter assembly 4 has such a thickness that when it is placed in position in the disposable sample receiver 3, it will press the removable strip or foil 33 sealingly against the bottom outlet 302 of the receiving chamber 301, but yet permit the protrusion 211 of the pivotal lid 21 to pull the removable strip or foil 33 away from the bottom outlet to empty the receiving chamber 301 on the closing of the lid 21.

A reagent, which shifts color upon presence of the biomarker, may be provided in the flow path 32 and is then located in or downstream of the permeable member 4. When present, it is always located in the detection compartment 321, suitably in the lowermost detection filter 42 if such a one is provided.

To make a color shift in the detection compartment 321 directly visible, the bottom member 31 of the disposable sample receiver 3 may be transparent or just have a transparent portion 314 right under the detection compartment 321 as shown in FIG. 8. If desired, also the top member 30 may be made of transparent material. To assist the user of the detector assembly 1 in assessing any possible color shift in the detection compartment 321, it is preferred that the detector housing 2 as shown in FIG. 2 comprises an electronic camera 23 for taking a photo of the detection compartment 321 through the transparent portion 314 of the bottom member 31. The detector housing 2 further comprises a CPU 26, a display 22 and generally also at least one USB port 27. The photo is transmitted to the CPU 26, which after processing the data passes them on to the display 22. Preferably, a sensor (not shown) senses the closing of the lid 21 and sends a signal to the CPU 26 to start a timer when the lid protrusion 211 pulls away the removable strip or foil 33 from the bottom outlet 302 to empty the receiving chamber 301.

In this way, the exact point of time when the sample is passed on to the reagent (by removing the separating member 33 from the bottom outlet 302 of the receiving chamber 301) can be controlled, in combination with the depression 303 that is adapted to receive any excess volume for which there is no room in the receiving chamber 301 so that the analyzed amount of the sample is exactly the same each time an analysis is carried out, a high degree of repeatability and accuracy is achieved, and thereby also a fail-safe system.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is applicable for use in detection of the presence of a biomarker or the like in a sample of a flowable substance, e.g. a powder or a liquid, usually a body fluid, such as blood, urine, or saliva, for example.

The invention claimed is:

1. A method of detecting the presence of a biomarker in a sample of a flowable substance, the method comprising the steps of
   providing a disposable sample receiver (3) having a receiving chamber (301), a bottom outlet (302) from the receiving chamber (301), a flow path (32) leading away from the bottom outlet (302), a reagent within said flow path (32), and a directly visible detection compartment (321);
   disposing the sample in the receiving chamber (301) and permitting the flowable substance to pass through the bottom outlet (302) into the flow path (32);
   providing a depression (303) surrounding the receiving chamber (301);
   filling the receiving chamber (301) until an excess of the flowable substance spills over into the depression (303);
   emptying the receiving chamber (301) by removing, from the bottom outlet (302), a separating member (33) that is impermeable to the flowable substance, the separating member (33) being configured to, prior to removal, prevent flow from the receiving chamber (301) through the bottom outlet (302) and into the flow path (32); and
   detecting the presence of a biomarker in said sample of the flowable substance by means of an electronic camera (23).

2. A method as claimed in claim 1, wherein said flow path (32) comprises a permeable member (4) configured to prevent passage of at least one component of the flowable substance and permit passage of one other of the at least one components of the flowable substance.

3. A method as claimed in claim 1, wherein:
   said directly visible detection compartment (321) is located at the opposite end of said flow path (32) compared to the bottom outlet (302), and
   said detection compartment (321) is provided with a reagent which shifts color upon presence of a biomarker in the sample of flowable substance.

4. A method as claimed in claim 2, wherein:
   the flowable substance is whole blood, and
   the permeable member (4) separates blood cells from plasma containing the biomarker.

5. A method as claimed in claim 3, wherein the reagent is located in or downstream of the permeable member (4).

6. A method as claimed in claim 5, further comprising the steps of:
   analyzing the color shift by means of the electronic camera (23) and software (in 26), and
   showing a result of the analysis on a display (22).

7. A disposable sample receiver (3) for use in detection of the presence of a biomarker in a sample of a flowable substance, said disposable sample receiver (3) comprising:
   a receiving chamber (301) for reception of the sample of the flowable substance;
   a bottom outlet (302) from the receiving chamber (301);
   a flow path (32) leading away from the bottom outlet (302);
   a reagent within said flow path (32);
   a directly visible detection compartment (321);
   a depression (303) surrounding the receiving chamber (301), the depression (303) being dimensioned to receive a predetermined volume, said depression (303) receiving any excess volume for which there is no room in the receiving chamber (301); and
   a removable separating member (33) impermeable to the flowable substance and disposed at the bottom outlet (302) to keep the bottom outlet (302) sealed, said separating member (33), upon removal, connecting the receiving chamber (301) to the flow path (32).

8. A disposable sample receiver (3) as claimed in claim 7, wherein said directly visible detection compartment (321) is located at the opposite end of said flow path (32) compared to the bottom outlet (302).

9. A disposable sample receiver (3) as claimed in claim 8, wherein the flow path (32) at least upstream of the detection compartment (321) is provided with a permeable member (4), which prevents passage of at least one component of the flowable substance but permits passage of another one of the at least one components of the flowable substance.

10. A disposable sample receiver (3) as claimed in claim 9, wherein a reagent, which shifts color upon presence of the biomarker, is provided in said flow path (32).

11. A disposable sample receiver (3) as claimed in claim 10, wherein the reagent is located in or downstream of the permeable member (4).

12. A disposable sample receiver (3) as claimed in claim 11, wherein the permeable member (4) includes an uppermost receiving filter (40), at least one separation filter (41), and a lowermost detection filter (42) that contains the reagent and is located in the detection compartment (321).

13. A detector assembly (1) for use in detection of the presence of a biomarker in a sample of a flowable substance, said assembly (1) comprising:
   a portable detector housing (2) having a place (25) for reception of a disposable sample receiver (3);
   an electronic camera (23) for detecting the presence of the biomarker in the sample of the flowable substance;

a disposable sample receiver (3) for said sample of the flowable substance, the disposable sample receiver (3) being configured to be located in said place (25), wherein:

said disposable sample receiver (3) comprises: a receiving chamber (301) for reception of the sample of flowable substance; a bottom outlet (302) from the receiving chamber (301); a flow path (32) leading away from the bottom outlet (302); a reagent within said flow path (32); a directly visible detection compartment (321), a depression (303) surrounding the receiving chamber (301), the depression (303) being dimensioned to receive a predetermined volume, said depression (303) receiving any excess volume for which there is no room in the receiving chamber (301); and a removable separating member (33) impermeable to the flowable substance and disposed at the bottom outlet (302) to keep the bottom outlet (302) sealed, said separating member (33), upon removal from the bottom outlet (302), connecting the receiving chamber (301) to the flow path (32); and said detector housing (2) comprises a device (21) for removing the separating member (33) from the bottom outlet (302) of the receiving chamber (301) to activate the disposable sample receiver (3).

14. A detector assembly (1) as claimed in claim 13, wherein said directly visible detection compartment (321) is located at the opposite end of said flow path (32) compared to the bottom outlet (302).

15. A detector assembly (1) as claimed in claim 14, wherein the flow path (32) at least upstream of the detection compartment (321) is provided with a permeable member (4), which prevents passage of at least one component of the flowable substance but permits passage of another one.

16. A detector assembly (1) as claimed in claim 15, wherein a reagent, which shifts color upon presence of the bio marker, is provided in said flow path (32).

17. A detector assembly (1) as claimed in claim 16, wherein the reagent is located in or downstream of the permeable member (4).

18. A detector assembly (1) as claimed in claim 17, wherein the permeable member (4) includes an uppermost receiving filter (40), at least one separation filter (41), and a lowermost detection filter (42) that contains the reagent and is located in the detection compartment (321).

19. A detector assembly (1) as claimed in claim 13, wherein:

the detector housing (2) comprises equipment for analyzing color change marks of the bio marker to be detected, and said equipment comprises the electronic camera (23), software (in 26), and a display (22) for displaying the result of the analysis.

20. A detector assembly (1) as claimed in claim 13, wherein:

the disposable sample receiver (3) includes a top member (30) and a bottom member (31), the top member (30) has wall portions defining side walls of the receiving chamber (301), and the removable separating member is an elongate strip (33) having one end (332) closing the bottom outlet (302) by forming a bottom of the receiving chamber (301) and the other end (331) fixed to a body portion (305, 312) of the disposable sample receiver (3), the disposable sample receiver (3) having an internal support (311) for the strip (33), and the internal support (311) being spaced from the fixed end (331) of the strip (33) to form between them a space (313) under the strip (33), the space (313) having a depth that is sufficient to permit the strip (33) to be pressed into the space (313) a distance that will pull the strip (33) away from the bottom outlet (3) in order to empty the sample of flowable substance into the flow path (32).

21. A detector assembly (1) as claimed in claim 20, wherein:

the top member (30) of the disposable sample receiver (3) has an opening (304) located above the space (313), and a device for pulling the sealing end (332) of the strip (33) away from the bottom outlet (302) includes a pivotal member (21) on the detector housing (2) provided with a protrusion (211) adapted to enter the opening (304) in order to press down the strip (33) to remove the strip (33) from the bottom outlet (302) and thereby let the flowable substance flow into the flow path (32).

22. A detector assembly (1) as claimed in claim 21, wherein the pivotal member is a lid (21) that on shutting will cover the disposable sample receiver (3) and simultaneously pull away the strip (33) from the bottom outlet (302) to let the sample of flowable substance flow into the flow path (32), whereby every sample to be analyzed will be subjected to the same testing conditions with regard to volume and timing.

* * * * *